United States Patent
Chavan et al.

(10) Patent No.: US 9,790,223 B2
(45) Date of Patent: Oct. 17, 2017

(54) PROCESS FOR PREPARATION OF SODIUM (2S,5R)-6-(BENZYLOXY)-7-OXO-1,6-DIAZABICYCLO[3.2.1]OCTANE-2-CARBOXYLATE

(71) Applicant: WOCKHARDT LIMITED, Aurangabad, Maharashtra (IN)

(72) Inventors: Vijay Prakash Chavan, Sangli (IN); Karuna Suresh Wankhede, Aurangabad (IN); Vikas Vithalrao Deshmukh, Ahmednagar (IN); Satish Bhavsar, Aurangabad (IN); Kiran Ramchandra Patil, Jalgaon (IN); Ravindra Dattatraya Yeole, Aurangabad (IN); Prasad Keshav Deshpande, Aurangabad (IN); Mahesh Vithalbhai Patel, Aurangabad (IN)

(73) Assignee: WOCKHARDT LIMITED, Chikalthana, Aurangabad (IN)

( * ) Notice: Subject to any disclaimer, the term of this patent is extended or adjusted under 35 U.S.C. 154(b) by 0 days.

(21) Appl. No.: 15/125,554

(22) PCT Filed: Mar. 12, 2015

(86) PCT No.: PCT/IB2015/051794
§ 371 (c)(1),
(2) Date: Sep. 12, 2016

(87) PCT Pub. No.: WO2015/136473
PCT Pub. Date: Sep. 17, 2015

(65) Prior Publication Data
US 2017/0008892 A1   Jan. 12, 2017

(30) Foreign Application Priority Data
Mar. 14, 2014  (IN) .......................... 858/MUM/2014

(51) Int. Cl.
| | | |
|---|---|---|
| C07D 471/08 | (2006.01) | |
| C07F 7/18 | (2006.01) | |
| C07C 251/36 | (2006.01) | |
| C07D 211/56 | (2006.01) | |
| C07C 249/08 | (2006.01) | |

(52) U.S. Cl.
CPC .......... *C07D 471/08* (2013.01); *C07C 249/08* (2013.01); *C07C 251/36* (2013.01); *C07D 211/56* (2013.01); *C07F 7/1852* (2013.01); *C07F 7/1856* (2013.01)

(58) Field of Classification Search
CPC ................................. C07D 471/08; C07F 7/18
USPC .................................................... 546/121, 14
See application file for complete search history.

(56) References Cited

U.S. PATENT DOCUMENTS

| | | |
|---|---|---|
| 2012/0053350 A1 | 3/2012 | Mangion et al. |
| 2012/0165533 A1 | 6/2012 | Abe et al. |
| 2012/0323010 A1 | 12/2012 | Ronsheim et al. |

FOREIGN PATENT DOCUMENTS

| | | |
|---|---|---|
| WO | 2013/149136 A1 | 10/2013 |
| WO | 2014/135929 A1 | 9/2014 |
| WO | 2015/052682 A1 | 4/2015 |

*Primary Examiner* — Charanjit Aulakh
(74) *Attorney, Agent, or Firm* — Bio Intelelctual Property Services LLC (Bio IPS); O. (Sam) Zaghmout

(57) ABSTRACT

A process for preparation of a compound of Formula (I) is disclosed.

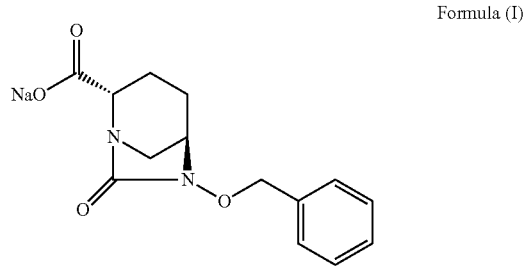

Formula (I)

10 Claims, No Drawings

PROCESS FOR PREPARATION OF SODIUM (2S,5R)-6-(BENZYLOXY)-7-OXO-1,6-DIAZABICYCLO[3.2.1]OCTANE-2-CARBOXYLATE

RELATED PATENT APPLICATIONS

This application claims priority to Indian Patent Application No. 858/MUM/2014 filed on Mar. 14, 2014, the disclosures of which are incorporated herein by reference in its entirety as if fully rewritten herein.

FIELD OF THE INVENTION

The invention relates to a process for preparation of sodium (2S, 5R)-6-(benzyloxy)-7-oxo-1,6-diazabicyclo[3.2.1]octane-2-carboxylate.

BACKGROUND OF INVENTION

A compound of Formula (I), chemically known as sodium (2S, 5R)-6-(benzyloxy)-7-oxo-1,6-diazabicyclo[3.2.1]octane-2-carboxylate, can be used as an intermediate in the synthesis of several antibacterial compounds and is disclosed in PCT International Patent Application No. PCT/IB2013/059264. The present invention discloses a process for preparation of a compound of Formula (I).

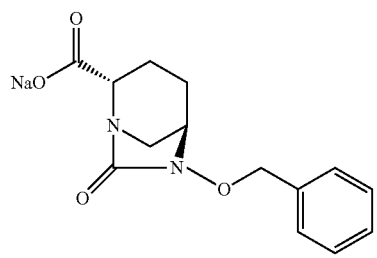

Formula (I)

SUMMARY OF THE INVENTION

In one general aspect, there is provided a process for preparation of a compound of Formula (I),

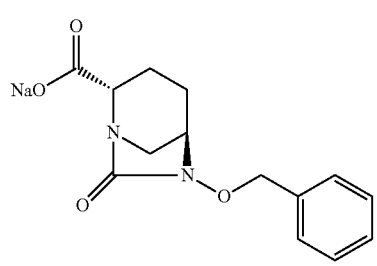

Formula (I)

said process comprising:

(a) reacting a compound of Formula (II) with trimethylsulfoxonium iodide to obtain a compound of Formula (III); wherein $P_1$ is H or amine protecting group and $P_2$ is H or alcohol protecting group;

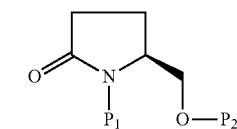

Formula (II)

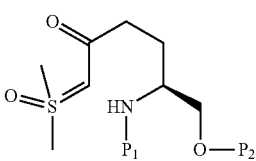

Formula (III)

(b) reacting a compound of Formula (III) with O-benzyl hydroxylamine hydrochloride to obtain a compound of Formula (IV); wherein $P_1$ and $P_2$ are as defined above;

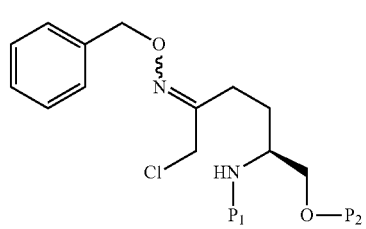

Formula (IV)

(c) cyclizing a compound of Formula (IV) to obtain a compound of Formula (V); wherein $P_1$ and $P_2$ are as defined above;

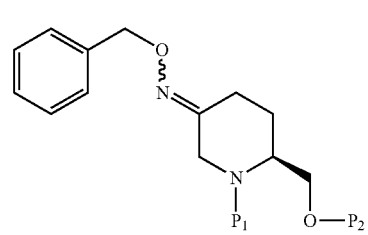

Formula (V)

(d) reducing a compound of Formula (V) to obtain a compound of Formula (VI); wherein $P_1$ and $P_2$ are as defined above;

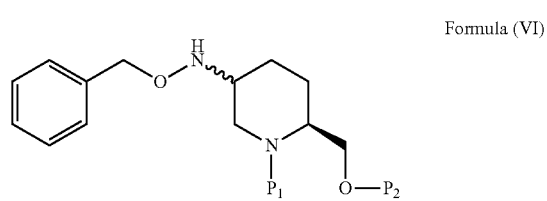

Formula (VI)

(e) converting a compound of Formula (VI) to a compound of Formula (VII); wherein $P_2$ is as defined above;

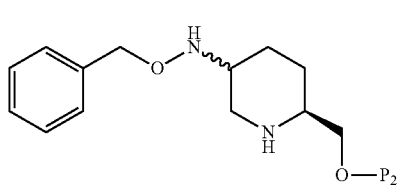

Formula (VII)

(f) cyclizing a compound of Formula (VII) to obtain a compound of Formula (VIII), optionally followed by diastereomeric separation; wherein $P_2$ is as defined above;

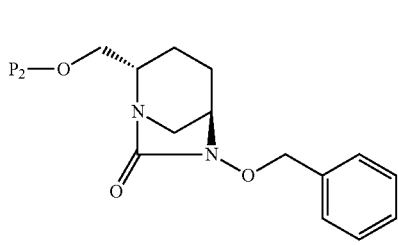

Formula (VIII)

(g) deprotecting a compound of Formula (VIII) to obtain a compound of Formula (IX); and

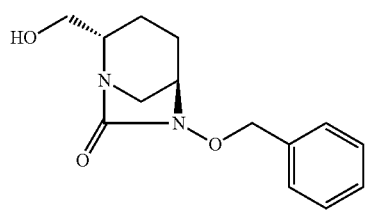

Formula (IX)

(h) oxidizing a compound of Formula (IX), followed by sodium salt formation to obtain a compound of Formula (I).

The details of one or more embodiments of the inventions are set forth in the description below. Other features, objects and advantages of the inventions will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, which would occur to one skilled in the relevant art and having possession of this disclosure, are to be considered within the scope of the invention. It must be noted that, as used in this specification and the appended claims, the singular forms "a", "an", and "the" include plural referents unless the content clearly dictates otherwise. All references including patents, patent applications, and literature cited in the specification are expressly incorporated herein by reference in their entirety.

In one general aspect, there is provided a process for preparation of a compound of Formula (I),

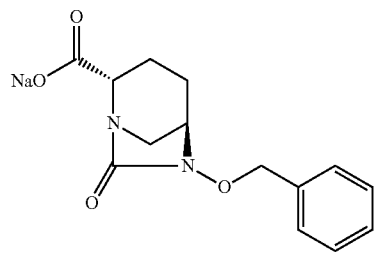

Formula (I)

said process comprising:

(a) reacting a compound of Formula (II) with trimethylsulfoxonium iodide to obtain a compound of Formula (III); wherein $P_1$ is H or amine protecting group and $P_2$ is H or alcohol protecting group;

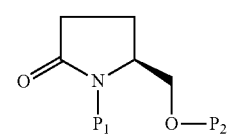

Formula (II)

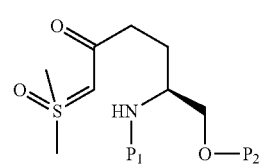

Formula (III)

(b) reacting a compound of Formula (III) with O-benzyl hydroxylamine hydrochloride to obtain a compound of Formula (IV); wherein $P_1$ and $P_2$ are as defined above;

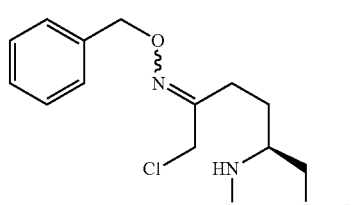

Formula (IV)

(c) cyclizing a compound of Formula (IV) to obtain a compound of Formula (V); wherein $P_1$ and $P_2$ are as defined above;

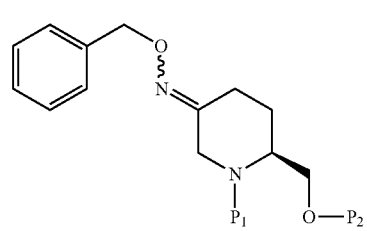

Formula (V)

(d) reducing a compound of Formula (V) to obtain a compound of Formula (VI); wherein P₁ and P₂ are as defined above;

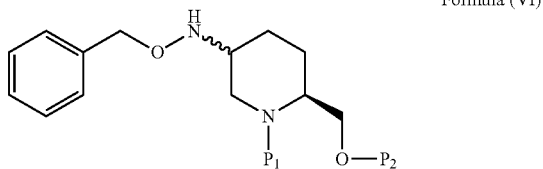

Formula (VI)

(e) converting a compound of Formula (VI) to a compound of Formula (VII); wherein P₂ is as defined above;

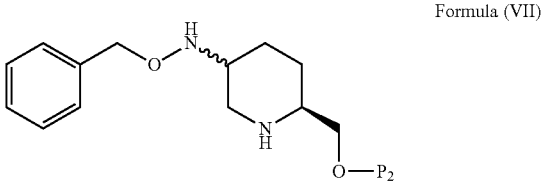

Formula (VII)

(f) cyclizing a compound of Formula (VII) to obtain a compound of Formula (VIII), optionally followed by diastereomeric separation; wherein P₂ is as defined above;

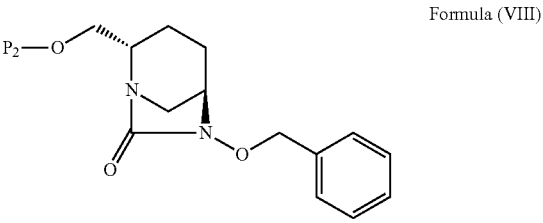

Formula (VIII)

(g) deprotecting a compound of Formula (VIII) to obtain a compound of Formula (IX); and

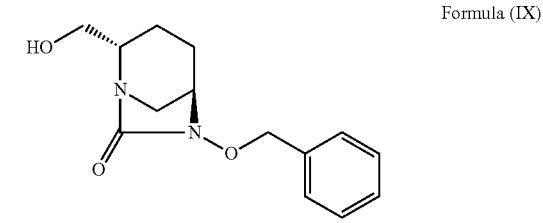 [SMILES: O=C1N2C[C@@H](CC[C@H]2CO)N1OCc1ccccc1]

Formula (IX)

(h) oxidizing a compound of Formula (IX), followed by sodium salt formation to obtain a compound of Formula (I).

In some embodiments, a compound of Formula (I) is prepared by using a general procedure described in Scheme 1. Typically, a compound of Formula (I) is prepared from double protected pyrrolidin-2-one alcohol (II), wherein $P_1$ is hydrogen or amine protecting group and $P_2$ is hydrogen or alcohol protecting group. Typical, non-limiting examples of amine protecting groups include carbobenzyloxy, p-methoxybenzyl carbonyl, tert-butyloxycarbonyl, 9-fluorenylmethyloxycarbonyl, acetyl, benzoyl, benzyl, carbamate, p-methoxybenzyl, 3,4-dimethoxybenzyl, p-methoxyphenyl, tosyl and the like. Typical, non-limiting examples of alcohol protecting groups include acetyl, benzoyl, benzyl, beta-methoxyethoxymethyl ether, dimethoxytrityl, methoxymethyl ether, dimethoxytrityl, p-methoxybenzyl ether, methylthiomethyl ether, pivaloyl, tetrahydropyranyl, tetrahydrofuran, trityl, alkyl silyl ether, alkyl aryl silyl ether, methyl ether, ethoxyethyl ether and the like. In some embodiments, a compound of Formula (I) is prepared from a compound of Formula (II), wherein $P_1$ is tert-butyloxycarbonyl and $P_2$ is tert-butyldimethylsilyl.

A compound of Formula (II) is subjected to ring opening to obtain a compound of Formula (III). The compound of Formula (II) is reacted with the anion generated from trimethylsulfoxonium iodide and suitable base such as sodium hydride or potassium tert-butoxide, in a suitable organic solvent such as tetrahydrofuran, dioxane, diethyl ether, diisopropyl ether or a mixture thereof at a temperature ranging from about −20° C. to 40° C. to provide a ring opened compound of Formula (III). In some embodiments, the compound of Formula (II) is reacted with trimethylsulfoxonium iodide in presence of sodium hydride and tetrahydrofuran at a temperature ranging from about −20° C. to 0° C. to obtain a compound of Formula (III).

A compound of Formula (III) is subjected to imine formation reaction by reacting with O-benzyl hydroxylamine hydrochloride in a suitable organic solvent such as tetrahydrofuran, dioxane, diethyl ether, diisopropyl ether, ethyl acetate or a mixture thereof at a temperature ranging from about 25° C. to 80° C. to provide a chloroimine intermediate (IV). In some embodiments, a compound of Formula (III) is reacted with O-benzyl hydroxylamine hydrochloride in presence of tetrahydrofuran a temperature ranging from about 50° C. to 60° C. to obtain a compound of Formula (IV).

The chloroimine compound of Formula (IV) is subjected to ring closing reaction in the presence of suitable base such as sodium hydride, potassium tert-butoxide, n-butyl lithium and the like, in a suitable organic solvent such as tetrahydrofuran, dioxane, diethyl ether, diisopropyl ether, ethyl acetate or a mixture thereof at a temperature ranging from about −20° C. to 40° C., to provide a substituted piperidine compound of Formula (V). In some embodiments, compound of Formula (IV) is treated with potassium tert-butoxide in tetrahydrofuran a temperature ranging from about −10° C. to 0° C. to obtain a compound of Formula (V).

A compound of Formula (V) is reduced by action of a suitable reducing agent in presence of a suitable acid such as acetic acid or propionic acid and a suitable organic solvent such as dichloromethane, chloroform, tetrahydrofuran, dioxane, ethyl acetate or a mixture thereof at a temperature ranging from about 0° C. to 40° C. to provide a ring amine compound of Formula (VI). Typical, non-limiting examples of reducing agents include sodium borohydride, sodium cyanoborohydride, sodium triacetoxyborohydride, sodium tripropanoyloxyborohydride, lithium borohydride and the like. In some embodiments, compound of Formula (V) is reacted with sodium cyanoborohydride in presence of acetic acid and dichloromethane at a temperature ranging from about 25° C. to 35° C. temperature to obtain a compound of Formula (VI).

The protecting group at piperidine nitrogen of a compound of Formula (VI) is removed by the action of a suitable deprotecting agent in presence of a suitable organic solvent at a temperature ranging from about 0° C. to 40° C. to provide a dibasic compound of Formula (VII). Typical, non-limiting examples of deprotecting agents include inorganic acid such as hydrochloric acid, trifluoroacetic acid, hydrobromic acid or sulfuric acid; Lewis acid such as boron trifluoride etherate complex; base such as piperidine, ammonia or methylamine; ammonium cerium (IV) nitrate; hydrogen source over transition metal catalyst; and the like. Typical, non-limiting examples of suitable solvent include dichloromethane, chloroform, tetrahydrofuran, dioxane, ethyl acetate or a mixture thereof. In some embodiments, a compound of Formula (VI) is reacted with boron trifluoride etherate complex in presence of dichloromethane at a temperature of about 25° C. to 35° C. to obtain a compound of Formula (VII).

A compound of Formula (VII) is treated with a suitable cyclizing agent in presence of a suitable base and solvent at a temperature ranging from about −20° C. to 40° C. to furnish a cyclized urea intermediate in 50:50 diastereomeric purity. Typical, non-limiting examples of cyclizing agents include triphosgene, phosgene, carbonyldiimidazole and the like. Typical, non-limiting examples of suitable base include diisopropylethylamine, triethylamine, pyridine and the like. In some embodiments, compound of Formula (VII) is reacted with triphosgene in presence of diisopropylethylamine and acetonitrile at a temperature ranging from about −20° C. to 0° C. to obtain a compound of Formula (VIII) in 50:50 diastereomeric purity. The diastereomeric separation is done by crystallizing the diastereomeric mixture in suitable solvent such as n-hexane, cyclohexane, heptane, methyl alcohol, ethyl alcohol, isopropyl alcohol, water or a mixture thereof to provide a pure (2S, 5R) diastereomer. In some embodiments, compound of Formula (VIII) in 50:50 diastereomeric purity is crystallized with n-hexane to obtain a pure (2S, 5R) diastereomer of a compound of Formula (VIII). In some embodiments, compound of Formula (I) is prepared from (2S,5R)-6-benzyloxy-2-(tert-butyl-dimethylsilyl-oxymethyl)-7-oxo-1,6-diaza-bicyclo-[3.2.1] octane.

The alcohol protecting group in a compound of Formula (VIII) is removed to obtain a compound of Formula (IX). In some embodiments, a compound of Formula (VIII) is reacted with a suitable deprotecting reagent in presence of a suitable solvent at a temperature ranging from about 0° C. to 40° C. to provide an alcoholic compound of Formula (IX). Typical, non-limiting examples of deprotecting agents include acid, base, hydrogen source over transition metal catalyst, oxidizing agent, reducing agent, fluoride ion such as sodium fluoride, tetra-n-butylammonium fluoride, hydrogen fluoride-pyridine complex, hydrogen fluoride-triethylamine complex, trimethylsilyl iodide and the like. Typical, non-limiting examples of a suitable solvent include tetrahydrofuran, dioxane, chloroform, diisopropyl ether or a mixture thereof. In some embodiments, compound of Formula (VIII) is reacted with tetra n-butylammonium fluoride, in presence of tetrahydrofuran at a temperature ranging from about 25° C. to 35° C. to obtain a compound of Formula (IX).

The alcoholic compound of Formula (IX) is oxidized and then the oxidized compound is subjected to sodium salt formation to obtain a compound of Formula (I). The compound of Formula (IX) is first treated with Des Martin periodinane to provide an intermediate aldehyde, which is further oxidized by treating immediately with cyclohexene, sodium hypophosphate and sodium chlorite mixture in tert-butyl alcohol and water mixture at a temperature ranging from about 0° C. to 50° C. The reaction mixture without any isolation is subsequently subjected to sodium salt formation to obtain the compound of Formula (I). In some embodiments, sodium salt formation is achieved by either treating with sodium 2-ethyl hexanoate or by contacting with a sodium exchange resin to obtain sodium salt of (2S, 5R)-6-benzyloxy-7-oxo-1,6-diaza-bicyclo[3.2.1]-octane-2-carboxylic acid (I).

Scheme 1

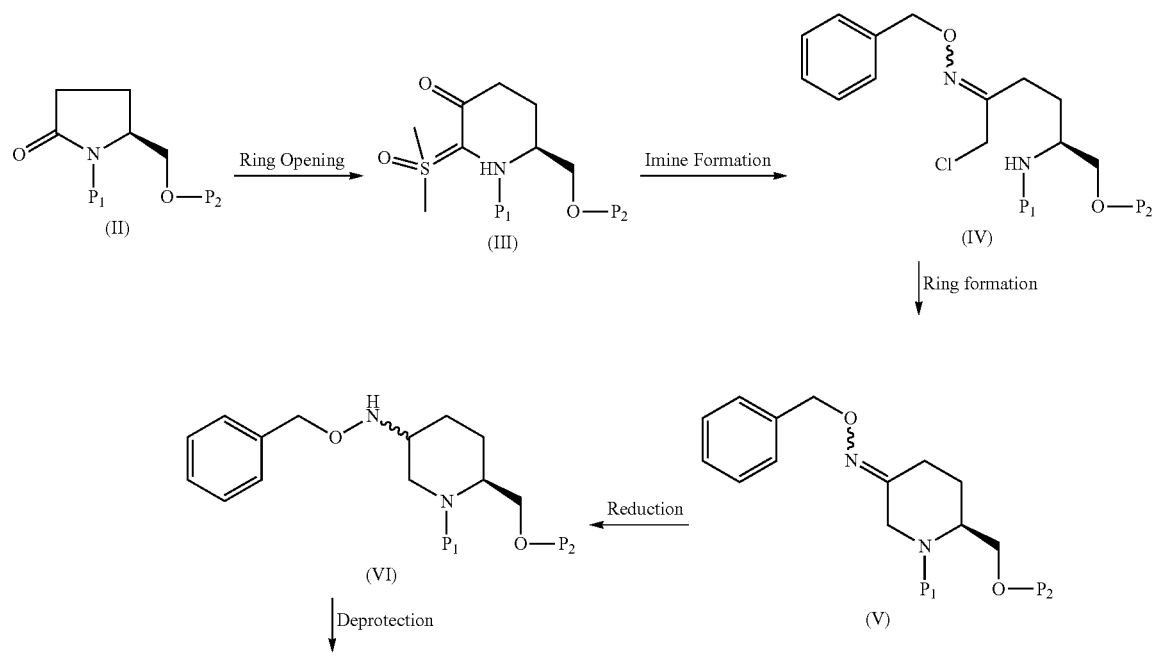

-continued

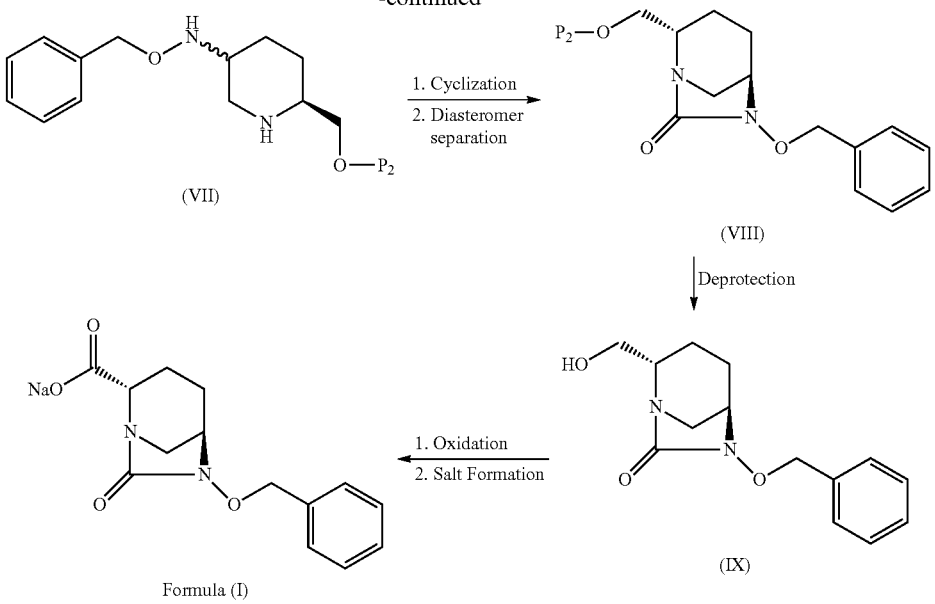

In some embodiments, compound of Formula (I) is prepared using a process described in Scheme 1.

In some embodiments, compound of Formula (I) is prepared using a process described in Scheme 1, wherein $P_1$ is tert-butyloxycarbonyl and $P_2$ is tert-butyldimethylsilyl.

In some embodiments, there is provided a compound of Formula (IV); wherein $P_2$ is H or an alcohol protecting group.

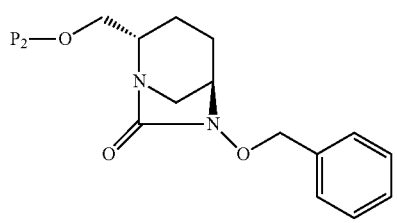

Formula (IV)

In some embodiments, there is provided a compound of Formula (VII); wherein $P_2$ is H or an alcohol protecting group.

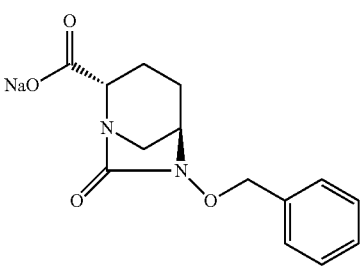

Formula (VII)

In some embodiments, there is provided a compound of Formula (VIII); wherein $P_2$ is H or an alcohol protecting group.

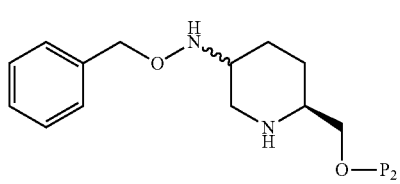

Formula (VIII)

In some embodiments, there is provided a process for preparation of a compound of Formula (I),

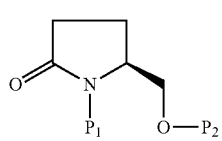

Formula (I)

said process comprising:

(a) reacting a compound of Formula (II) with trimethylsulfoxonium iodide to obtain a compound of Formula (III); wherein $P_1$ is tert-butyloxycarbonyl and $P_2$ is tert-butyldimethylsilyl;

Formula (II)

-continued

Formula (III)

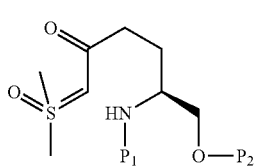

(b) reacting a compound of Formula (III) with O-benzyl hydroxylamine hydrochloride to obtain a compound of Formula (IV); wherein $P_1$ and $P_2$ are as defined above;

Formula (IV)

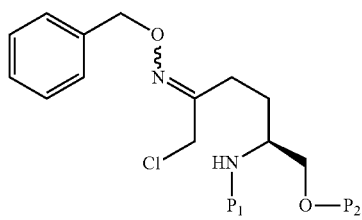

(c) cyclizing a compound of Formula (IV) in presence of potassium tert-butoxide to obtain a compound of Formula (V); wherein $P_1$ and $P_2$ are as defined above;

Formula (V)

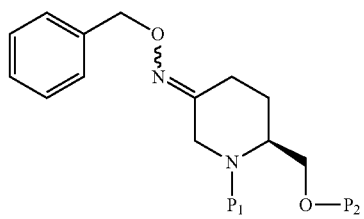

(d) reducing a compound of Formula (V) in presence of sodium cyanoborohydride to obtain a compound of Formula (VI); wherein $P_1$ and $P_2$ are as defined above;

Formula (VI)

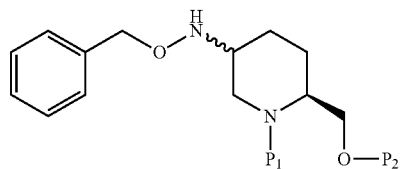

(e) deprotecting a compound of Formula (VI) in presence of boron trifluoride etherate complex to obtain a compound of Formula (VII); wherein $P_2$ is as defined above;

Formula (VII)

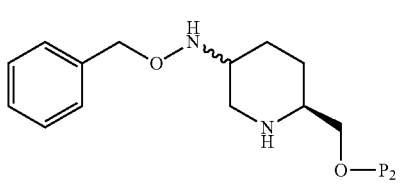

(f) cyclizing a compound of Formula (VII) in presence of triphosgene to obtain a compound of Formula (VIII), optionally followed by diastereomeric separation; wherein $P_2$ is as defined above;

Formula (VIII)

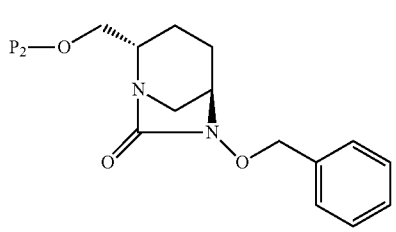

(g) deprotecting a compound of Formula (VIII) in presence of tetra n-butylammonium fluoride to obtain a compound of Formula (IX); and Formula (IX)

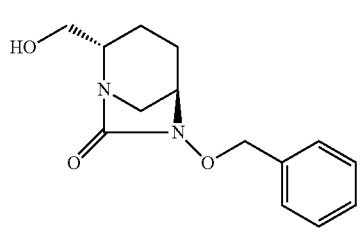

(h) oxidizing a compound of Formula (IX), followed by sodium salt formation to obtain a compound of Formula (I).

In some embodiments, there is provided a compound of Formula (VIII), wherein $P_2$ is tert-butyldimethylsilyl, having diastereomeric purity of at least 99% as determined by HPLC.

Formula (VIII)

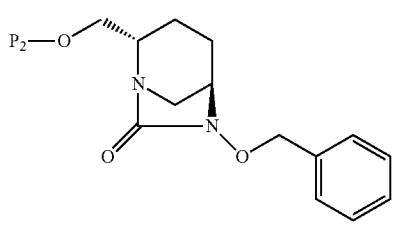

In some embodiments, there is provided a process for preparation of a compound of Formula (I) having purity of at least about 97% as determined by HPLC.

In some embodiments, there is provided a compound of Formula (I) having a purity of at least 97% as determined by HPLC.

In some embodiments, there is provided a pharmaceutical composition comprising a compound of Formula (I) having a purity of at least about 97% as determined by HPLC. In some embodiments, pharmaceutical composition may further comprise one or more pharmaceutically acceptable excipients.

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

Synthesis of sodium (2S, 5R)-6-(benzyloxy)-7-oxo-1,6-diazabicyclo[3.2.1]octane-2-carboxylate Step 1: Preparation of S-[1-[(tert-butyldimethylsilyl)-oxymethyl]-5-[dimethyl(oxido)-λ-4-sulfanylidene]-4-oxo-pentyl]-carbamic acid tert-butyl ester (III)

To a suspension of trimethylsulfoxonium iodide (180.36 gm, 0.819 mol) in tetrahydrofuran (900 ml), sodium hydride (32.89 g, 0.819 mol, 60% in mineral oil) was charged in one portion at 30° C. temperature. The reaction mixture was stirred for 15 minutes and then dropwise addition of dimethylsulphoxide (1.125 ml) was done over a period of 3 hours at room temperature to provide a white suspension. The white suspension was added to a pre-cooled a solution of 2-(tert-butyldimethylsilyl-oxymethyl)-5-oxo-pyrrolidine-1-carboxylic acid tert-butyl ester (II) (225 g, 0.683 mol, prepared as per J. Org Chem.; 2011, 76, 5574 and WO2009067600) in tetrahydrofuran (675 ml) and triethylamine (123.48 ml, 0.887 mol) mixture at −13° C. by maintaining the reaction mixture temperature below −10° C. The resulting suspension was stirred for additional 1 hour at −10° C. The reaction mixture was carefully quenched by addition of saturated aqueous ammonium chloride (1.0 L) at −10° C. to 10° C. The reaction was extracted by adding ethyl acetate (1.5 L). The layers were separated and aqueous layer was re-extracted with ethyl acetate (500 ml×3). The combined organic layer was washed successively with saturated aqueous sodium bicarbonate (1.0 L), water (2.0 L) followed by saturated aqueous sodium chloride solution (1.0 L). Organic layer was dried over sodium sulfate and evaporated under vacuum to provide 265 g of S-[1-[(tert-butyldimethylsilyl)-oxymethyl]-5-[dimethyl(oxido)-λ-4-sulfanylidene]-4-oxo-pentyl]-carbamic acid tert-butyl ester (III) as a yellow oily mass.

Analysis:
Mass: 422.3 (M+1); for Molecular weight: 421.68 and Molecular Formula: $C_{19}H_{39}NO_5SSi$;
$^1H$ NMR ($CDCl_3$): δ 4.77 (br d, 1H), 4.38 (br s, 1H), 3.58 (br s, 3H), 3.39 (s, 3H), 3.38 (s, 3H), 2.17-2.27 (m, 2H), 1.73-1.82 (m, 2H), 1.43 (s, 9H), 0.88 (s, 9H), 0.01 (s, 3H), 0.04 (s, 3H).

Step 2: Preparation of S-[4-benzyloxyimino-1-(tert-butyldimethylsilyl-oxymethyl)-5-chloro-pentyl]-carbamic acid tert-butyl ester (IV)

To a suspension of S-[1-[(tert-butyldimethylsilyl)-oxymethyl]-5-[dimethyl(oxido)-λ-4-sulfanylidene]-4-oxo-pentyl]-carbamic acid tert-butyl ester (III) (440.0 g, 1.045 mol) in tetrahydrofuran (6.6 L), O-benzhydroxylamine hydrochloride (200.0 g, 1.254 mol) was charged. The reaction mixture was heated to 50° C. for 2.5 hours. The reaction mixture was filtered through pad of celite and filtrate was concentrated to provide a residue. The residue was dissolved in ethyl acetate (5.0 L) and washed successively with saturated aqueous sodium bicarbonate (1.5 L), water (1.5 L) and saturated aqueous sodium chloride (1.5 L). Organic layer was dried over sodium sulfate. Solvent was evaporated under vacuum to yield 463.0 g of S-[4-benzyloxyimino-1-(tert-butyldimethylsilyl-oxymethyl)-5-chloro-pentyl]-carbamic acid tert-butyl ester (IV) as an oily mass.

Analysis:
Mass: 486.1 (M+1); for Molecular weight: 485.4 and Molecular Formula: $C_{24}H_{41}N_2O_4SiCl$;
$^1H$ NMR ($CDCl_3$): δ 7.26-7.36 (m, 5H), 5.10 (s, 2H), 4.66 (br d, 1H), 3.58-4.27 (m, 2H), 3.56-3.58 (m, 3H), 2.40-2.57 (m, 2H), 1.68-1.89 (m, 2H), 1.44 (s, 9H), 0.89 (s, 9H), 0.02 (s, 3H), 0.04 (s, 3H).

Step 3: Preparation of S-5-benzyloxyimino-2-(tert-butyldimethylsilyl-oxymethyl)-piperidine-1-carboxylic acid tert-butyl ester (V)

To a solution of S-[4-benzyloxyimino-1-(tert-butyldimethylsilyl-oxymethyl)-5-chloro-pentyl]-carbamic acid tert-butyl ester (IV) (463.0 g 0.954 mol) in tetrahydrofuran (6.9 L), was charged potassium tert-butoxide (139.2 g, 1.241 mol) in portions over a period of 30 minutes by maintaining temperature −10° C. The resulting suspension was stirred for additional 1.5 hours at −10° C. to −5° C. The reaction mixture was quenched by addition of saturated aqueous ammonium chloride (2.0 L) at −5° C. to 10° C. The organic layer was separated and aqueous layer was extracted with ethyl acetate (1.0 L×2). The combined organic layer was washed with saturated aqueous sodium chloride solution (2.0 L). Organic layer was dried over sodium sulfate, and then evaporated under vacuum to yield 394.0 g of S-5-benzyloxyimino-2-(tert-butyldimethylsilyl-oxymethyl)-piperidine-1-carboxylic acid tert-butyl ester (V) as an yellow oily mass.

Analysis:
Mass: 449.4 (M+1) for Molecular weight: 448.68 and Molecular Formula: $C_{24}H_{40}N_2O_4Si$;
$^1H$ NMR ($CDCl_3$): δ 7.25-7.33 (m, 5H), 5.04-5.14 (m, 2H), 4.35 (br s, 1H), 3.95 (br s, 1H), 3.63-3.74 (br d, 2H), 3.60-3.63 (m, 1H), 2.70-2.77 (m, 1H), 2.33-2.41 (m, 1H), 1.79-1.95 (m, 2H), 1.44 (s, 9H), 0.88 (s, 9H), 0.03 (s, 3H), 0.04 (s, 3H).

Step 4: Preparation of (2S,5RS)-5-benzyloxyamino-2-(tert-butyldimethylsilyl-oxymethyl)-piperidine-1-carboxylic acid tert-butyl ester (VI)

To a solution of S-5-benzyloxyimino-2-(tert-butyldimethylsilyl-oxymethyl)-piperidine-1-carboxylic acid tert-butyl ester (V) (394.0 g, 0.879 mol) in dichloromethane (5.0 L) and glacial acetic acid (788 ml), was charged sodium cyanoborohydride (70.88 g, 1.14 mol) one portion. The resulting reaction mixture was stirred at temperature of about 25° C. to 30° C. for 2 hours. The mixture was quenched with adding aqueous solution of sodium bicarbonate (1.3 kg) in water (5.0 L). The organic layer was separated and aqueous layer was extracted with dichloromethane (2.0 L). The combined organic layer washed successively with water (2.0 L), saturated aqueous sodium chloride (2.0 L) and dried over sodium sulfate. Solvent was evaporated under vacuum to provide a residue. The residue was purified by silica gel column chromatography to yield 208 g of (2S,5RS)-5-benzyloxyamino-2-(tert-butyldimethylsilyl-oxymethyl)-piperidine-1-carboxylic acid tert-butyl ester (VI) as pale yellow liquid.

Analysis:

Mass: 451.4 (M+1); for Molecular weight: 450.70 and Molecular Formula: $C_{24}H_{42}N_2O_4Si$;

$^1$H NMR (CDCl$_3$): δ 7.26-7.36 (m, 5H), 4.90-5.50 (br s, 1H), 4.70 (dd, 2H), 4.09-4.25 (m, 2H), 3.56-3.72 (m, 2H), 2.55-3.14 (m, 2H), 1.21-1.94 (m, 4H), 1.45 (s, 9H), 0.89 (s, 9H), 0.05 (s, 6H).

Step 5: Preparation of (2S,5RS)-5-benzyloxyamino-2-(tert-butyldimethylsilyl-oxymethyl)-piperidine (VII)

To a solution of S-5-benzyloxyamino-2-(tert-butyldimethylsilyl-oxymethyl)-piperidine-1-carboxylic acid tert-butyl ester (VI) (208 g, 0.462 mol) in dichloromethane (3.0 L), boron trifluoride diethyletherate complex (114.15 ml, 0.924 mol) was charged in one portion. The resulting reaction mixture was stirred at temperature of about 25° C. to 35° C. temperature for 2 hours. The reaction mixture was quenched with saturated aqueous sodium bicarbonate (2.0 L). The organic layer was separated and aqueous layer was extracted with dichloromethane (1.5 L×2). The combined organic layer was washed with saturated aqueous sodium chloride (1.0 L) and dried over sodium sulfate. Solvent was evaporated under vacuum to yield 159 g of (2S,5RS)-5-benzyloxyamino-2-(tert-butyldimethylsilyl-oxymethyl)-piperidine (VII) as a yellowish syrup.

Analysis:

Mass: 351.3 (M+1); for Molecular weight: 350.58 and Molecular Formula: $C_{19}H_{34}N_2O_2Si$.

Step-6: Preparation of (2S,5R)-6-benzyloxy-2-(tert-butyl-dimethylsilyl-oxymethyl)-7-oxo-1,6-diaza-bicyclo-[3.2.1]octane (VIII)

Part 1: Preparation of (2S,5RS)-6-benzyloxy-2-(tert-butyl-dimethylsilyl-oxymethyl)-7-oxo-1,6-diaza-bicyclo-[3.2.1]octane To a solution of (2S,5RS)-5-benzyloxyamino-2-(tert-butyldimethylsilyl-oxymethyl)-piperidine (VII) (159.0 g, 0.454 mol) in a mixture of acetonitrile (2.38 L) and diisopropylethylamine (316.5 ml, 1.81 mol) was added triphosgene (59.27 gm, 0.199 mol) dissolved in acetonitrile (760 ml) at −15° C. over 30 minutes under stirring. The resulting reaction mixture was stirred for additional 1 hour at −10° C. The reaction mixture was quenched by addition of saturated aqueous sodium bicarbonate (2.0 L) at −5° C. to 10° C. Acetonitrile was evaporated from the reaction mixture under vacuum and to the left over aqueous phase, dichloromethane (2.5 L) was added. The organic layer was separated and aqueous layer was extracted with dichloromethane (1.5 L×2). The combined organic layer was washed successively with water (2.0 L), saturated aqueous sodium chloride (2.0 L) and dried over sodium sulfate. Solvent was evaporated under vacuum and the residue was passed through a silica gel bed to yield 83.0 g of diastereomeric mixture (2S, 5RS)-6-benzyloxy-2-(tert-butyl-dimethylsilyl-oxymethyl)-7-oxo-1, 6-diaza-bicyclo-[3.2.1]octane in 50:50 ratio as a yellow liquid.

Part-2: Separation of diastereomers to prepare (2S, 5R)-6-benzyloxy-2-(tert-butyl-dimethylsilyl-oxymethyl)-7-oxo-1,6-diaza-bicyclo-[3.2.1]octane A mixture of diastereomers (2S,5RS)-6-benzyloxy-2-(tert-butyl-dimethylsilyl-oxymethyl)-7-oxo-1,6-diaza-bicyclo[3.2.1]octane in 50:50 ratio (47.0 gm, 0.125 mol), was dissolved in n-hexane (141 ml) and stirred at temperature of about 10° C. to 15° C. for 1 hour. Precipitated solid was filtered and washed with n-hexane (47 ml) to provide 12.0 g of diastereomerically pure (2S,5R)-6-benzyloxy-2-(tert-butyl-dimethylsilyl-oxymethyl)-7-oxo-1,6-diaza-bicyclo-[3.2.1] octane (VIII) as a white crystalline material.

Analysis:

Mass: 377.3 (M+1); for Molecular weight: 376.58 and Molecular Formula: $C_{20}H_{32}N_2O_3Si$;

$^1$H NMR (CDCl$_3$): δ 7.33-7.44 (m, 5H), 4.95 (dd, 2H), 3.76-3.85 (ddd, 2H), 3.37-3.40 (m, 1H), 3.28-3.31 (m, 2H), 2.89 (brd, 1H), 1.90-2.02 (m, 2H), 1.62-1.74 (m, 2H), 1.56 (s, 9H), 0.06 (s, 3H), 0.05 (s, 3H).

Diastereomeric purity as determined by HPLC: 99.85%

Step-7: Preparation of (2S,5R)-6-benzyloxy-2-hydroxymethyl)-7-oxo-1,6-diaza-bicyclo-[3.2.1]octane (IX)

To a solution of (2S,5R)-6-benzyloxy-2-(tert-butyl-dimethylsilyl-oxymethyl)-7-oxo-1,6-diaza-bicyclo-[3.2.1]octane (VIII) (12.0 g, 31.9 mmol) in tetrahydrofuran (180 ml) was charged tetra n-butyl ammonium fluoride (38.0 ml, 38 mmol, 1 M in tetrahydrofuran) at room temperature. The reaction mixture was stirred for 2 hours. It was quenched with saturated aqueous ammonium chloride (100 ml). The organic layer was separated and aqueous layer extracted with dichloromethane (150 ml×3). The combined organic layer was washed with saturated aqueous sodium chloride (150 ml), dried over sodium sulfate and evaporated under vacuum to yield 24.0 g of (2S,5R)-6-benzyloxy-2-hydroxymethyl)-7-oxo-1,6-diaza-bicyclo-[3.2.1]octane (IX) as a yellow liquid. The compound of Formula (IX) was purified by silica gel (60-120 mesh) column chromatography using a mixture of ethyl acetate and hexane as an eluent.

Analysis:

Mass: 263.1 (M+1); for Molecular weight: 262.31 and Molecular Formula: $C_{14}H_{18}N_2O_3$ $^1$H NMR (CDCl$_3$): δ 7.34-7.42 (m, 5H), 4.95 (dd, 2H), 3.67-3.73 (m, 1H), 3.53-3.60 (m, 2H), 3.32-3.34 (m, 1H), 2.88-3.01 (m, 2H), 2.09 (brs, 1H), 1.57-2.03 (m, 2H), 1.53-1.57 (m, 1H), 1.37-1.40 (m, 1H).

Step 8: Preparation of sodium salt of (2S, 5R)-6-benzyloxy-7-oxo-1,6-diaza-bicyclo[3.2.1]-octane-2-carboxylic acid (I)

Step I:

Compound of Formula (IX) obtained in step 8 above was used without any further purification. To the clear solution of (2S,5R)-6-benzyloxy-2-hydroxymethyl)-7-oxo-1,6-diaza-bicyclo-[3.2.1]octane (IX) (24.0 g, 31.8 mmol) (quantities added based upon theoretical basis i.e 8.3 g) in dichloromethane (160 ml), was added Dess-Martin reagent (24.1 g, 57.24 mmol) in portions over 15 minutes. The resulting suspension was stirred for 2 hours at 25° C. The reaction was quenched by adding a solution, prepared from saturated aqueous sodium hydrogen carbonate solution (160 ml) and 72.0 g of sodium thiosulfate. Diethyl ether (160 ml) was added to the reaction mixture and it was stirred for 5-10 minutes and filtered through celite. Biphasic layer from filtrate was separated. Organic layer was washed with saturated aqueous sodium hydrogen carbonate solution (160 ml) followed by saturated aqueous sodium chloride solution (160 ml). Organic layer was dried over sodium sulfate and evaporated to dryness at 30° C. to obtain 20.0 g of intermediate aldehyde, which was used immediately for the next reaction.

Step II:

To the crude intermediate aldehyde (20.0 g, 31.6 mmol) (quantities added based upon theoretical yield i.e. 8.2 g) obtained as above, was charged t-butyl alcohol (160 ml) and cyclohexene (10.8 ml, 110.6 mmol). The reaction mixture was cooled to temperature of about 10° C. to 15° C. To this mixture was added clear solution prepared from sodium hypophosphate (14.8 g, 94.8 mmol) and sodium chlorite (5.7 g, 63.2 mmol) in water (82.0 ml) over a period of 30 minutes by maintaining temperature between 10° C. to 15° C. The reaction mixture was further stirred for 1 hour and was quenched with saturated aqueous ammonium chloride solution. The reaction mixture was subjected to evaporation under vacuum at 40° C. to remove t-butyl alcohol. Resulting mixture was extracted with dichloromethane (3×150 ml). Layers were separated. Combined organic layer was washed with aqueous brine solution, dried over sodium sulfate and evaporated to dryness under vacuum to obtain 16.0 g of crude residue. To this residue was added acetone (83 ml) to provide a clear solution and to it was added dropwise a solution of sodium 2-ethyl hexanoate (4.5 g) in acetone (24 ml). The reaction mixture was stirred for 15 hours at 25° C. to 30° C. to provide a suspension. To the suspension was added diethyl ether (215 ml) and stirred for 30 minutes. Resulting solid was filtered over suction, and wet cake was washed with cold acetone (83 ml) followed by diethyl ether (83 ml). The solid was dried under vacuum at 40° C. to provide 3.6 g of off-white colored, non-hygroscopic sodium salt of (2S, 5R)-6-benzyloxy-7-oxo-1,6-diaza-bicyclo[3.2.1]-octane-2-carboxylic acid (I).

Analysis:

Mass: 275.2 as M−1 (for free acid) for Molecular Weight: 298 and Molecular Formula: $C_{14}H_{15}N_2O_4Na$;

NMR (DMSO-$d_6$): δ 7.43-7.32 (m, 5H), 4.88 (q, 2H), 3.48 (s, 1H), 3.21 (d, 1H), 2.73 (d, 1H), 2.04-2.09 (m, 1H), 1.77-1.74 (m, 1H), 1.65-1.72 (m, 1H), 1.55-1.59 (m, 1H);

Purity as determined by HPLC: 97.47%;

$[\alpha]_D^{25}$: −42.34° (c 0.5, water).

The invention claimed is:

1. A process for preparation of a compound of Formula (I),

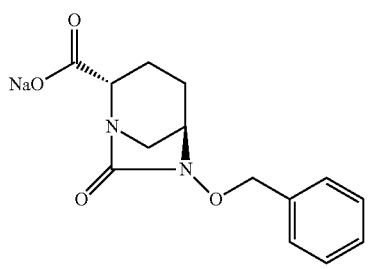

Formula (I)

said process comprising:

(a) reacting a compound of Formula (II) with trimethylsulfoxonium iodide to obtain a compound of Formula (III); wherein $P_1$ is H or an amine protecting group and $P_2$ is H or an alcohol protecting group;

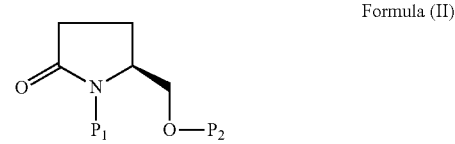

Formula (II)

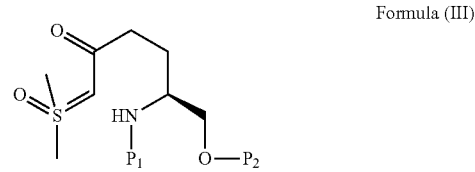

Formula (III)

(b) reacting a compound of Formula (III) with O-benzyl hydroxylamine hydrochloride to obtain a compound of Formula (IV); wherein $P_1$ and $P_2$ are as defined above;

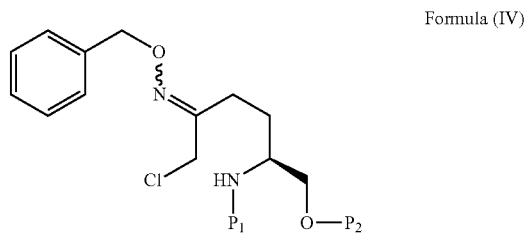

Formula (IV)

(c) cyclizing a compound of Formula (IV) to obtain a compound of Formula (V); wherein $P_1$ and $P_2$ are as defined above;

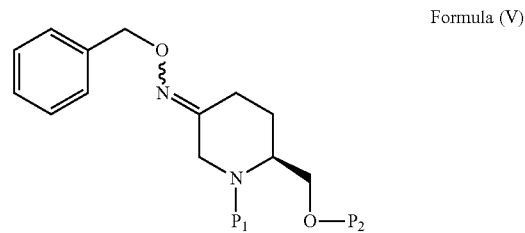

Formula (V)

(d) reducing a compound of Formula (V) to obtain a compound of Formula (VI); wherein $P_1$ and $P_2$ are as defined above;

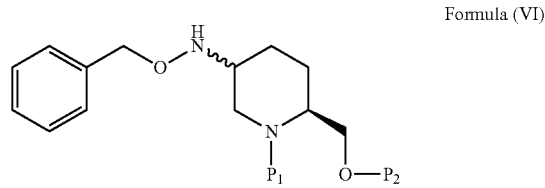

Formula (VI)

(e) converting a compound of Formula (VI) to a compound of Formula (VII); wherein P₂ is as defined above;

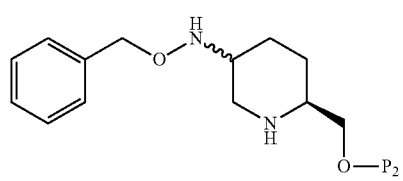

Formula (VII)

(f) cyclizing a compound of Formula (VII) to obtain a compound of Formula (VIII), optionally followed by diastereomeric separation; wherein P₂ is as defined above;

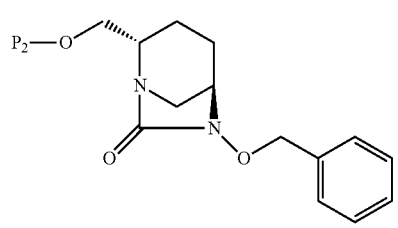

Formula (VIII)

(g) deprotecting a compound of Formula (VIII) to obtain a compound of Formula (IX); and

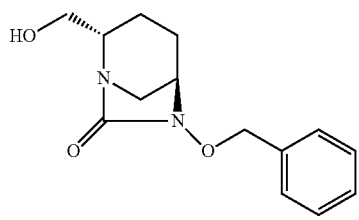

Formula (IX)

(h) oxidizing a compound of Formula (IX), followed by sodium salt formation to obtain a compound of Formula (I).

2. The process according to claim 1, wherein the P₁ is tert-butoxycarbonyl and P₂ is tert-butyldimethylsilyl.

3. The process according to claim 1, wherein a compound of Formula (V) is obtained by cyclizing a compound of Formula (IV) in presence of a base selected from a group consisting of sodium hydride, potassium tert-butoxide and n-butyl lithium.

4. The process according to claim 1, wherein a compound of Formula (VI) is obtained by reducing a compound of Formula (V) in presence of a reducing agent selected from a group consisting of sodium borohyride, sodium cyanoborohydride, sodium triacetoxyborohydride, sodium tripropanoyloxyborohydride and lithium borohydride.

5. The process according to claim 1, wherein a compound of Formula (VII) is obtained by treating a compound of Formula (VI) with a deprotecting agent selected from a group consisting of hydrochloric acid, trifluoroacetic acid, hydrobromic acid, sulphuric acid, boron trifluoride etherate complex, piperidine, ammonia, methylamine, ammonium cerium (IV) nitrate and hydrogen source in presence of a transition metal catalyst.

6. The process according to claim 1, wherein a compound of Formula (VIII) is obtained by cyclizing a compound of Formula (VII) in presence of a reagent selected from the group consisting of triphosogene, phosgene or carbonyldiimidazole.

7. The process according to claim 1, wherein the diastereomeric separation of compound of Formula (VIII) is obtained by carrying out crystallization in a solvent selected from a group consisting of n-hexane, cyclohexane, heptanes, methyl alcohol, ethyl alcohol, isopropyl alcohol, water or a mixture thereof.

8. The process according to claim 1, wherein sodium salt formation in step (h) is carried out in presence of sodium-2-ethyl hexanoate.

9. A process for preparation of a compound of Formula (I),

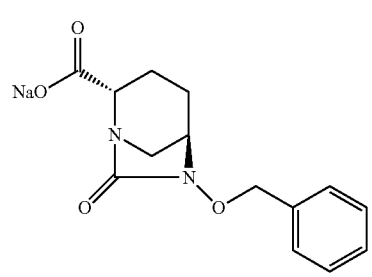

Formula (I)

said process comprising:
(a) reacting a compound of Formula (II) with trimethylsulfoxonium iodide to obtain a compound of Formula (III); wherein P₁ is tert-butyloxycarbonyl and P₂ is tert-butyldimethylsilyl;

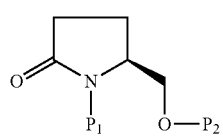

Formula (II)

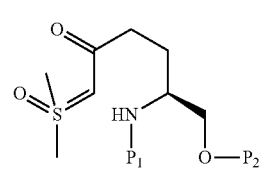

Formula (III)

(b) reacting a compound of Formula (III) with O-benzyl hydroxylamine hydrochloride to obtain a compound of Formula (IV); wherein P₁ and P₂ are as defined above;

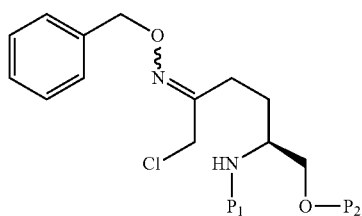

Formula (IV)

(c) cyclizing a compound of Formula (IV) in presence of potassium tert-butoxide to obtain a compound of Formula (V); wherein $P_1$ and $P_2$ are as defined above;

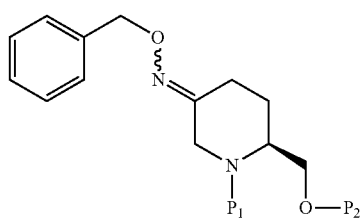

Formula (V)

(d) reducing a compound of Formula (V) in presence of sodium cyanoborohydride to obtain a compound of Formula (VI); wherein $P_1$ and $P_2$ are as defined above;

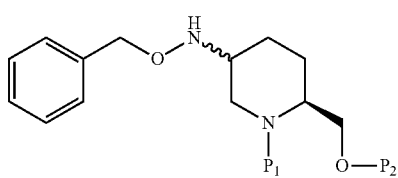

Formula (VI)

(e) deprotecting a compound of Formula (VI) in presence of boron trifluoride etherate complex to obtain a compound of Formula (VII); wherein $P_2$ is as defined above;

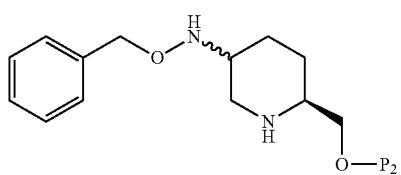

Formula (VII)

(f) cyclizing a compound of Formula (VII) in presence of triphosgene to obtain a compound of Formula (VIII), optionally followed by diastereomeric separation; wherein $P_2$ is as defined above;

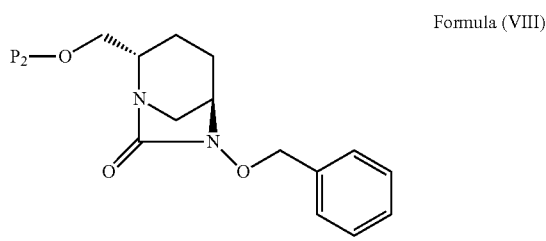

Formula (VIII)

(g) deprotecting a compound of Formula (VIII) in presence of tetra n-butylammonium fluoride to obtain a compound of Formula (IX); and

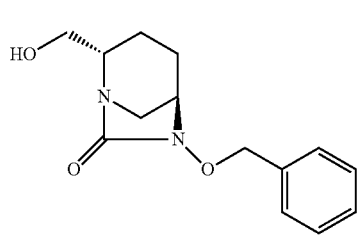

Formula (IX)

(h) oxidizing a compound of Formula (IX), followed by sodium salt formation to obtain a compound of Formula (I).

10. The compound of Formula (VIII) according to claim 9, wherein $P_2$ is tert-butyldimethylsilyl, having diastereomeric purity of at least 99% as determined by HPLC

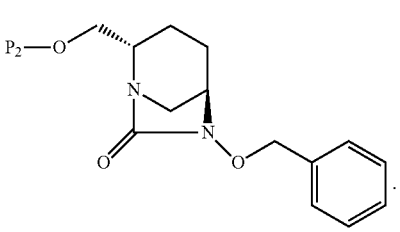

Formula (VIII)

* * * * *